US012741008B2

(12) United States Patent
Cunniff et al.

(10) Patent No.: US 12,741,008 B2
(45) Date of Patent: Sep. 22, 2026

(54) VITAMIN E AND CANCER THERAPEUTIC COMPOSITIONS AND METHODS

(71) Applicants: University of Vermont and State Agricultural College, Burlington, VT (US); RS Oncology, LLC, Cambridge, MA (US); Wake Forest University Health Sciences, Winston-Salem, NC (US)

(72) Inventors: Brian Cunniff, Burlington, VT (US); Gregory Frykman, Cambridge, MA (US); Kimberly Johnson Nelson, Winston-Salem, NC (US)

(73) Assignees: University of Vermont and State Agricultural College, Burlington, VT (US); RS Oncology, LLC, Cambridge, MA (US); Wake Forest University Health Sciences, Winston-Salem, NC (US)

(*) Notice: Subject to any disclaimer, the term of this patent is extended or adjusted under 35 U.S.C. 154(b) by 976 days.

(21) Appl. No.: 17/420,508

(22) PCT Filed: Jan. 6, 2020

(86) PCT No.: PCT/US2020/012423
§ 371 (c)(1),
(2) Date: Jul. 2, 2021

(87) PCT Pub. No.: WO2020/142782
PCT Pub. Date: Jul. 9, 2020

(65) Prior Publication Data

US 2022/0080025 A1 Mar. 17, 2022

Related U.S. Application Data

(60) Provisional application No. 62/788,332, filed on Jan. 4, 2019.

(51) Int. Cl.
*A61K 38/12* (2006.01)
*A61K 31/355* (2006.01)
*A61P 35/00* (2006.01)

(52) U.S. Cl.
CPC ............ *A61K 38/12* (2013.01); *A61K 31/355* (2013.01); *A61P 35/00* (2018.01)

(58) Field of Classification Search
CPC .... A61K 38/12; A61K 31/355; A61K 9/0019; A61K 31/136; A61K 45/06; A61K 47/20; A61P 35/00
See application file for complete search history.

(56) References Cited

U.S. PATENT DOCUMENTS

| | | | | |
|---|---|---|---|---|
| 3,551,554 | A | 12/1970 | Herschler | |
| 3,916,027 | A | 10/1975 | Taylor | |
| 2010/0120896 | A1* | 5/2010 | Sander | A61P 31/04 514/254.11 |
| 2013/0164379 | A1 | 6/2013 | Gartel et al. | |
| 2017/0227545 | A1* | 8/2017 | Mitchell | G01N 33/6848 |

FOREIGN PATENT DOCUMENTS

| | | | |
|---|---|---|---|
| CN | 101445803 | A | 6/2009 |
| WO | 2002/102400 | A1 | 12/2002 |
| WO | 2025/188940 | A1 | 9/2025 |

OTHER PUBLICATIONS

Newick (PLOS ONE, Jun. 2012, vol. 7, issue 6, 1-4) (Year: 2012).*
Levin (Analytical Microbiology, 1972, vol. II, pp. 347-354) (Year: 1972).*
Boutine et al, Cancer, Nov. 1, 1994, vol. 74, No. 9, 2460-2467 (Year: 1994).*
International Search Report and Written Opinion of the International Searching Authority dated Mar. 24, 2020 from corresponding International Patent Application No. PCT/US2020/012423 filed on Jan. 6, 2020.
Extended European Search Report issued Jul. 5, 2022 for European Patent Application No. 20736086.8 (9 pages).
Cunniff, et al., "Disabling Mitochondrial Peroxide Metabolism via Combinatorial Targeting of Peroxiredoxin 3 an an Effective Therapeutic Approach for Malignant Mesothelioma", PLOS ONE, May 26, 2015, p. 1-27.
Yang, et al., "Recent Advances in the Application of Vitamin E TPGS for Drug Delivery", Theranostics, vol. 8, issue 2, Jan. 1, 2018, pp. 464-485.
Tan, et al., "Recent developments in d-[alpha]-tocopheryl polyethylene glycol-succinate-based nanomedicine for cancer therapy", Drug Delivery, vol. 24, No. 1, Jan. 1, 2017, pp. 1831-1842.
O'Sullivan, S. M., et al. "Use of Tween 40 and Tween 80 to deliver a mixture of phytochemicals to human colonic adenocarcinoma cell (CaCo-2) monolayers." British journal of nutrition 91.5 (2004): 757-764.
Ragelle, H., et al., Nanoemulsion formulation of fisetin improves bioavailability and antitumour activity in mice. International Journal of Pharmaceutics, 2012, 427 (2), pp. 452-459. 10.1016/j.ijpharm.2012.02.025 . inserm-00709735.

(Continued)

*Primary Examiner* — Sudhakar Katakam
(74) *Attorney, Agent, or Firm* — Pierce Atwood LLP; Christopher A. Baxter

(57) ABSTRACT

The invention relates, in part, to compounds, compositions, and methods useful to treat cancer in cells and subjects. The invention relates, in part, to compounds, compositions, and methods useful to treat cancer in cells and subjects. According to one aspect of the invention, methods for reducing cell viability in a population cells comprising cancer cells are provided, the methods including: contacting a population of cells that include cancer cells with Thiostrepton (TS) and Vitamin E-TPGS, under conditions and for a period of time sufficient for a statistically significant reduction in viability in a plurality of the cancer cells.

8 Claims, 4 Drawing Sheets

(56) References Cited

OTHER PUBLICATIONS

Ujhelyi, Z., et al. "The enhanced inhibitory effect of different antitumor agents in self-microemulsifying drug delivery systems on human cervical cancer HeLa cells." Molecules 20.7 (2015): 13226-13239.

Fennell, Dean Anthony, et al., "First-In-Human Phase I Clinical Trial of RSO-021, a First-In Class Covalent Inhibitor of Mitochondrial Peroxiredoxin 3 (PRX3), in Patients with Malignant Pleural Effusion Due to Mesothelioma and Other Advanced Solid Tumors (MITOPE)", Journal of Clinical Oncology, vol. 42, No. 16, May 29, 2024.

Anderson et al., "The structure of thiostrepton." Nature, Jan. 17, 1970;225(5229):233-5.

Asikaer et al., "Thiostrepton: multifaceted biological activities and its applications in treatment of inflammatory diseases." Inflammopharmacology 33 (2025): 183-194.

Bagley et al., "Thiopeptide Antibiotics." Chemical Reviews 105 (2005): 685-714.

Bailly, "The bacterial thiopeptide thiostrepton. An update of its mode of action, pharmacological properties and applications." European Journal of Pharmacology 914 (2022): 174661.

Bren, "Animal Health and Consumer Protection", FDA Consumer Magazine, The Centennial Edition, Jan.-Feb. 2006.

Food and Drug Administration, "Q3C—Tables and List Guidance for Industry ." U.S. Department of Health and Human Services, Center for Drug Evaluation and Research (CDER), Center for Biologics Evaluation and Research (CBER), Jun. 2017, available online: https://www.fda.gov/media/71737/download.

Ghadi et al., "BCS class IV drugs: Highly notorious candidates for formulation development." Journal of Controlled Release 248 (2017): 71-95.

Just-Baringo et al., "Thiopeptide antibiotics: retrospective and recent advances." Marine Drugs 12 (2014): 317-351.

Lai et al., "Identification of thiostrepton as a novel inhibitor for psoriasis-like inflammation induced by TLR7-9." The Journal of Immunology 195 (2015): 3912-3921.

Levin et al., "Thiostrepton." Analytical Microbiology. Academic Press, 1972. 347-354.

Luo et al., "Thiostrepton alleviates experimental colitis by promoting RORγt ubiquitination and modulating dysbiosis." Cellular & Molecular Immunology 20 (2023): 1352-1366.

Newick et al., "Peroxiredoxin 3 is a redox-dependent target of thiostrepton in malignant mesothelioma cells." PloS One 7(6) (2012): e39404.

Pagano et al., "Thiostrepton, a new antibiotic. I. In vitro studies." Antibiotics Annual 3 (1955): 554-559.

Pestka et al., "The thiostrepton group of antibiotics." Mechanism of action of antimicrobial and antitumor agents. Berlin, Heidelberg: Springer Berlin Heidelberg, 1975. 551-573.

Scamp et al., "Co(III)-catalyzed C—H amidation of dehydroalanine for the site-selective structural diversification of thiostrepton." Angew Chem Int Ed Engl 59 (2020): 890-895.

Sharma et al., "In vitro antimalarial activity of novel semisynthetic nocathiacin I antibiotics." Antimicrobial Agents and Chemotherapy 59 (2015): 3174-3179.

Tan et al., "Recent developments in d-α-tocopheryl polyethylene glycol-succinate-based nanomedicine for cancer therapy." Drug Delivery 24 (2017): 1831-1842.

V A et al., "Formulation Strategy of BCS-II Drugs by Coupling Mechanistic In-Vitro and Nonclinical In-Vivo Data with PBPK: Fundamentals of Absorption-Dissolution to Parameterization of Modelling and Simulation." AAPS PharmSciTech 26 (2025): 106.

Vinogradov et al., "Introduction to thiopeptides: biological activity, biosynthesis, and strategies for functional reprogramming." Cell Chemical Biology 27 (2020): 1032-1051.

Walter et al., "Thiostrepton inhibits stable 70S ribosome binding and ribosome-dependent GTPase activation of elongation factor G and elongation factor 4." Nucleic Acids Research 40(1) (2012): 360-370.

Wang et al., "Micelle-encapsulated thiostrepton as an effective nanomedicine for inhibiting tumor growth and for suppressing FOXM1 in human xenografts." Mol Cancer Ther. Dec. 2011; 10(12): 2287-2297.

Wolf et al., "Structure-activity relationships of thiostrepton derivatives: implications for rational drug design." Journal of Computer-Aided Molecular Design 28 (2014): 1205-1215.

* cited by examiner

| | LP9 | HM | |
|---|---|---|---|
| IC50 | 0.0014920 | .0006045 | % |

| | LP9 | LP9/VitE-TPGS | |
|---|---|---|---|
| IC50 | 1.811 | 0.4112 | μM |

| | HM | HM/VitE-TPGS |
|---|---|---|
| IC50 | 0.7519 | 0.1262 |

μM

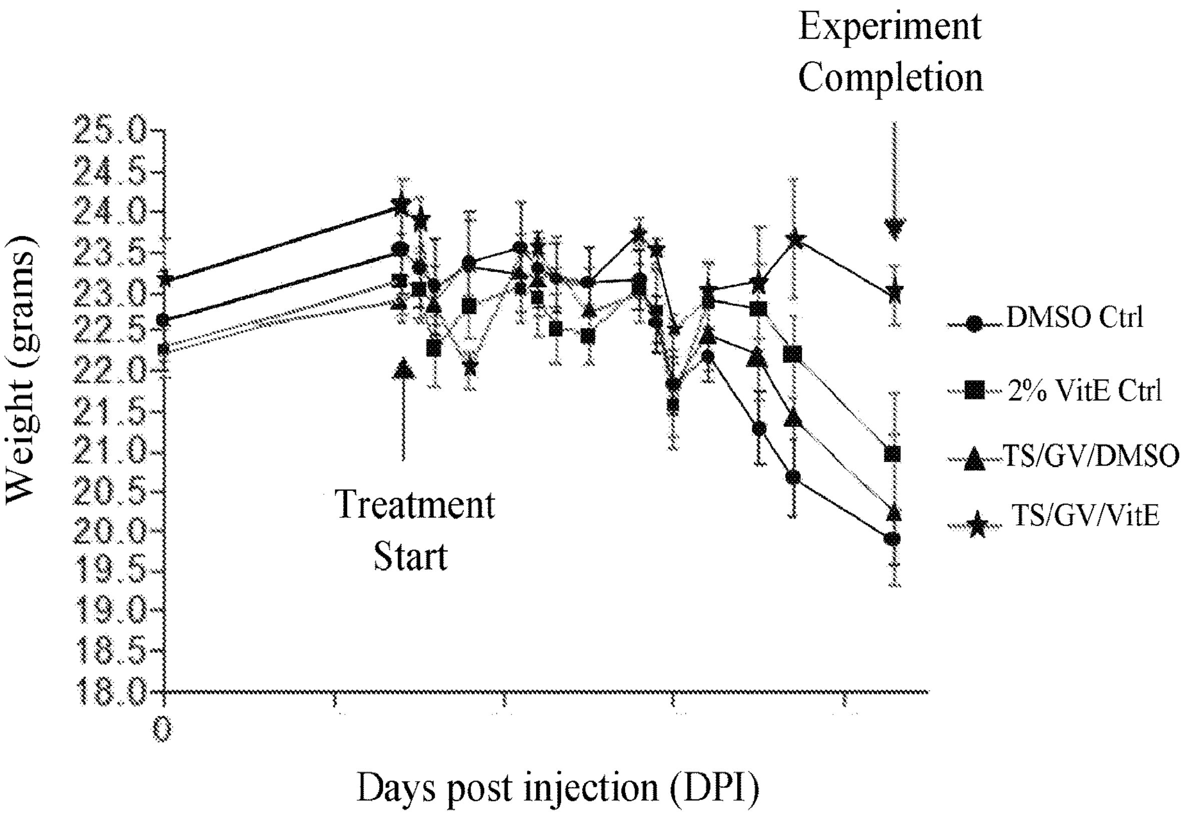
Figure 4
Figure 5
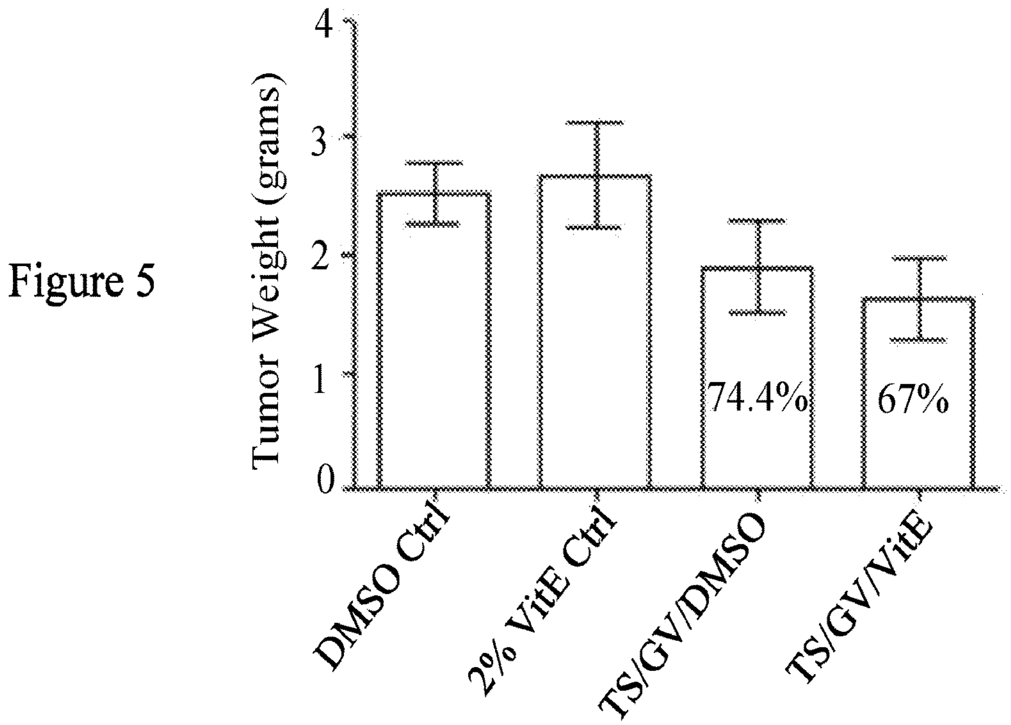

VITAMIN E AND CANCER THERAPEUTIC COMPOSITIONS AND METHODS

RELATED APPLICATIONS

This application claims priority under 35 U.S.C. § 371 to international application number PCT/US2020/012423, filed Jan. 6, 2020, which claims benefit under 35 U.S.C. § 119(e) of U.S. Provisional application Ser. No. 62/788,332 filed Jan. 4, 2019, the disclosure of each of which is incorporated by reference herein in its entirety.

FIELD OF THE INVENTION

The invention relates, in part, to compositions and methods for treating cancer, the methods including administration of compositions comprising Vitamin E.

BACKGROUND OF THE INVENTION

Treatment for various cancers may include administration of agents to kill cancer cells in a subject with the cancer. Current cancer treatments are limited by the relatively few compounds or agents that kill cancer cells and can be safely administered to cancer patients.

SUMMARY OF THE INVENTION

According to one aspect of the invention, methods for reducing cell viability in a population cells comprising cancer cells are provided, the methods including: contacting a population of cells that include cancer cells with Thiostrepton (TS) and Vitamin E-TPGS, under conditions and for a period of time sufficient for a statistically significant reduction in viability in a plurality of the cancer cells. In some embodiments, the method also includes providing a population of cells that includes cancer cells. In certain embodiments, the TS and Vitamin E-TPGS have a synergistic effect in reducing viability in the plurality of the cancer cells. In some embodiments, the contacting step further comprises contacting the cancer cells with gentian violet (GV). In certain embodiments, the contacting includes delivering a composition that includes the thiostrepton and Vitamin E-TPGS to the cancer cells. In some embodiments, the thiostrepton and Vitamin E-TPGS are delivered as part of a composition, wherein the composition optionally further includes one or more pharmaceutically acceptable carriers, and the composition optionally further includes dimethyl sulfoxide (DMSO). In certain embodiments, the cancer cells are in a subject, and the contacting includes administering the TS and Vitamin E-TPGS, and optionally the GV to the subject. In some embodiments, the administering includes systemic administration. In some embodiments, the systemic administration includes one or more of enteral administration and parenteral administration. In some embodiments, the quantity of TS administered in a 24 hour period ranges from 10 ng to 5 g. In some embodiments, the quantity of Vitamin E-TPGS administered in a 24 hour period ranges from 10 ng to 500 g. In some embodiments, the quantity of Vitamin E-TPGS administered to a subject in a single dose is at most 30 g. In some embodiments the Vitamin E-TPGS is administered in 1, 2, 3, 4, 5, or more doses per a 24 hour period. In some embodiments, the quantity of GV administered in a 24 hour period ranges from 10 ng to 200 mg. In some embodiments the amount of one or more of TS, Vitamin E-TPGS, and GV are each independently selected within and between each of one or more 24 hour periods. In certain embodiments, the contacting includes contacting with one or more compositions that include TS and Vitamin E-TPGS. In certain embodiments, the contacting includes contacting with one or more compositions that include TS and Vitamin E-TPGS. In certain embodiments, the contacting includes contacting with one or more compositions that include TS and Vitamin E-TPGS. In some embodiments, the method also includes contacting with a composition comprising GV. In some embodiments, the molar concentration of the TS in the composition is in a range from 10 nM to 5000 μM. In certain embodiments, the molar concentration of the GV in the composition is in a range from 10 nM to 500 μM. In some embodiments, the molar concentration of the Vitamin E-TPGS in the composition is in a range from 10 nM to 132 mM. In some embodiments, the one or more compositions further include one or more of a pharmaceutically acceptable carrier and excipient. In some embodiments, the cancer cells include malignant mesothelioma cells. In certain embodiments, the cancer cells include ovarian cancer cells. In some embodiments, the subject is a mammal, and optionally is a human. In some embodiments, the cancer cells are located in the subject in one or more of: the pleura of the lungs, the peritoneum, the pericardium, and the tunica vaginalis. In certain embodiments, the cancer cells are located in the subject in one or more of: the ovaries, the peritoneal cavity, peritoneal fluid, and the peritoneum. In some embodiments, the subject has a cancer presenting with a plural effusion. In certain embodiments, the subject has ovarian cancer. In certain embodiments, the subject has malignant mesothelioma. In some embodiments, a means of administering a composition of the invention comprises infusion into a body cavity of the subject. In some embodiments, the infusion means comprising using a catheter to administer the composition into a cavity of the subject. In some embodiments, the administration includes a primary treatment provided to the subject. In some embodiments, the subject additionally is administered one or more of a surgical regimen, a radiotherapy regimen, and a chemotherapy regimen. Vitamin E-TPGS is also referred to herein as: VitE and VitE-TPGS. In certain embodiments, Vitamin E is Vitamin E-TPGS.

According to another aspect of the invention, a compositions that includes Thiostrepton (TS) and Vitamin E-TPGS or a Vitamin E-TPGS functional derivative thereof is provided. In some embodiments, the composition includes Thiostrepton (TS) and Vitamin E-TPGS. In some embodiments, the composition also includes gentian violet (GV) or a GV functional derivative thereof. In some embodiments, the composition also includes dimethyl sulfoxide (DMSO). In certain embodiments, the molar concentration of the TS in the composition is in a range from 10 nM to 5000 μM. In some embodiments, the molar concentration of the GV or the GV functional derivative in the composition is in a range from 10 nM to 10 mM. In some embodiments, the molar concentration of the Vitamin E-TPGS or the Vitamin E-TPGS functional derivative in the composition is in a range from 10 nM to 140 mM. In some embodiments, the molar concentration of the Vitamin E-TPGS or the Vitamin E-TPGS functional derivative in the composition is in a range from 10 nM to 132 mM. In some embodiments, the composition also includes one or more of a pharmaceutically acceptable carrier and excipient. Vitamin E-TPGS is also referred to herein as: VitE and VitE-TPGS. In certain embodiments, the Vitamin E is Vitamin E-TPGS.

BRIEF DESCRIPTION OF THE DRAWINGS

FIG. 4 is a graph showing animal weights measured throughout the experiment. Note the significant weight loss in the last ~10 days in all groups except the TS/GV/VitE group. Due to extensive weight loss in control animals the experiment was terminated.

FIG. 5 is a histogram showing tumor weight from surgically resected tumor masses at 42 days post injection (DPI) following four injections of test compounds.

DETAILED DESCRIPTION

Figure 1:
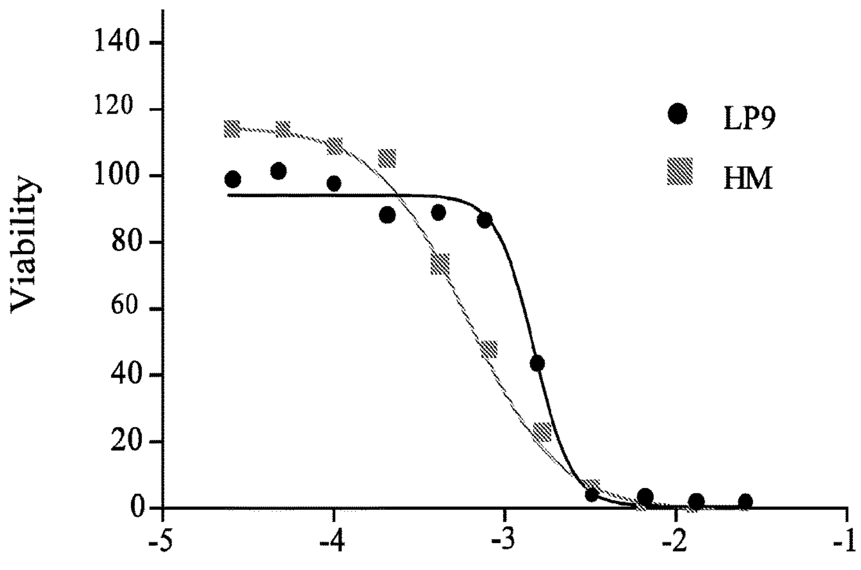
FIG. 1 is a graph showing results of studies that assessed sensitivity of LP9 and HM cells treated with VitE-TPGS for 48 hours. LP9 cells are non-tumorigenic, immortalized, mesothelial cells. HM cells are malignant mesothelioma cells.

It has now been determined that contacting cancer cells with a composition comprising Thiostrepton (TS) and Vitamin E-TPGS (also referred to herein as: VitE and VitE-TPGS) increases the cancer-cell killing effectiveness of the TS administration. It has now been identified that contacting a cancer cell with TS in solution with VitE potentiates the anti-cancer therapeutic effect of TS when compared with contacting a cancer cell with TS in the absence of VitE. Contacting a cancer cell or plurality of cancer cells with a composition comprising TS and VitE has now been found to have enhanced TS cancer cell killing efficacy, which increases the usefulness of TS as a cancer therapeutic agent. Although not wishing to be bound by a particular theory, the enhanced activity of the TS against cancer cells may result from increased availability of TS when in solution with VitE, thus permitting more cancer cell killing activity from the TS in the solution. Thus, the same amount of TS may have more cancer cell killing efficacy when in the presence of VitE than when not in the presence of VitE. Another benefit of the enhanced TS cell-killing activity when in solution with VitE is the ability to administer a lower dose of TS to a subject due to its increased efficacy in cancer cell killing. The increased activity of TS in VitE permits administration of lower amounts of TS, which may reduce side effects such as toxicity and/or other undesirable effects. Administering a composition comprising TS and VitE, optionally in combination with administering one of more of another cancer therapeutic compound such as GV and TLK-199, results in a synergistic effect of the cancer cell killing effects of the TS and the therapeutic compounds compared to the same treatments without inclusion of VitE. Administering a solution comprising TS and VitE TS and optionally administering one or more additional cancer therapeutic compounds to a cancer cell and/or a subject with cancer has been found to result in a synergistic treatment effect in which more cancer cell death results from the treatment than occurs when TS that is administered in solution without VitE. Certain aspects of the invention include contacting one or more cancer cells with a composition comprising TS and VitE as a treatment method for the cancer. An additional embodiment of the invention includes contacting one or more cancer cells with TS in VitE and also includes contacting the one or more cancer cells with another cancer therapeutic compound, such as but not limited to: GV, TLK-199, or another cancer therapeutic compound to treat the cancer in a cell, tissue, or subject.

Thiostrepton is an antibiotic compound that is also known by other names including, but not limited to: Bryamycin, Thiactin, alaninamide, HR4S203Y18, etc. VitE used in certain embodiments of methods and compositions of the invention is Vitamin E-TPGS, which is D-a-tocopheryl polyethylene glycol succinate, also referred to as D-a-tocopheryl polyethylene glycol 1000 succinate. As used herein the term VitE is used interchangeably with the terms VitE-TPGS and vitamin E-TPGS. Other Vitamin E compounds or modified forms may also be utilized in solution with TS in certain embodiments of the invention. Gentian violet (GV), also known as crystal violet and methyl violet, is a triphenylmethane dye with anti-bacterial, anti-fungal, anti-helminithic, anti-trypanosomal, anti-angiogenic and anti-tumor properties. TLK-199, chemical name: (S)-ethyl 2-amino-5-(((R)-3-(benzylthio)-1-(((S)-2-ethoxy-2-oxo-1-phenylethyl)amino)-1-oxopropan-2-yl)amino)-5-oxopentanoate, is also known as Ezatiostat hydrochloride. TLK-199 has been used as a treatment for bone marrow disorders, such as myelodysplastic syndrome (MDS).

The invention, in part, pertains to methods of contacting cancer cells with TS in a composition with VitE to treat cancer in cells, tissues, and subjects. Some compositions used in certain methods of the invention, such as a composition comprising TS in VitE, include one or more targeting agents or delivery agents. In certain embodiments of the invention treatment with a composition comprising TS and VitE comprises contacting one or more cancer cells with the agent or agents, wherein the contact results in the death of one or more of the contacted cancer cells. In certain aspects, the invention provides a composition comprising TS and VitE and one or more of GV, TLK-199, a targeting agent, and a cancer therapeutic compound. In certain aspects of the invention a composition that includes TS with VitE is administered to a subject and one or more compositions comprising one or more of GV, TLK-199, a targeting agent, and a cancer therapeutic compound is also administered to the subject. In certain aspects of an invention, a combination comprising a composition comprising TS in VitE and a composition comprising TLK-199 is administered to a cancer cell to treat the cancer. In certain embodiments of the invention, a combination of a composition comprising TS and VitE and at least one composition comprising one or more of GV, TLK-199, and another cancer therapeutic compound are administered to a cancer cell to treat the cancer.

Molecules, compounds, compositions, and methods of the invention may be used to treat a subject who has or is considered to be at risk of having a cancer. Thus, methods and compounds of the invention are useful to treat cancers in cells and in subjects. Cells that may be treated using a composition comprising TS and VitE include but are not limited to cancer cells. A cancer cell that is treated using a method, compound, or one or more compositions of the invention may be in vitro or in vivo. An in vivo cell is in a subject. As used herein the term "one or more" when used in reference to a cell means a single cell or a plurality of cells. A plurality of cells includes at least 2, 3, 4, 5, 6, 7, 8, 9, 10, 20, 50, 100, 500, 1,000, 5,000, 10,000, 50,000, 100,000, 500,000, 1,000,000, 5,000,000, 10,000,000, or more cells, including all integers in between. In some aspects of the invention a cell or plurality of cells is in cell culture or is in a subject. A plurality of cells may be a homogeneous or heterogeneous set of cells. As used herein, a homogeneous plurality of cells means a plurality of cells in which one or more cell characteristics of interest are the same for all of the cells in the plurality. It will be understood that a homogeneous plurality of cells may be considered to be homogeneous on the basis that each of the cells has the one or more characteristics of interest that are the same, for example are cancer cells, but the cells need not be entirely identical and features or characteristics, other than the characteristics of interest may differ in different cells of the plurality. In certain aspects of the invention, a plurality of cells is in a subject.

As used herein, a subject shall mean a vertebrate animal including but not limited to a human, mouse, rat, guinea pig, rabbit, cow, dog, cat, horse, goat, and non-human primate, e.g., monkey. In certain aspects of the invention, a subject may be a domesticated animal, a wild animal, or an agricultural animal. Thus, the invention can be used to treat diseases or conditions in human and non-human subjects. For instance, methods and compositions of the invention can be used in veterinary applications as well as in human prevention and treatment regimens. In some embodiments of the invention, the subject is a human. In some embodiments of the invention, a subject has one or more cancers. In some embodiments a subject exhibits, which is also referred to herein as "presents with," a plural effusion.

A composition comprising TS and VitE may be administered to a cell, tissue, and/or subject to treat one or more different types of cancer, including but not limited: a malignant mesothelioma, an ovarian cancer, a carcinoma, a sarcoma, a leukemia, a lymphoma, a myeloma, a glioma, breast cancer, an epithelial cancer, uterine cancer, vaginal cancer, prostate cancer, testicular cancer, penile cancer, colon cancer, rectal cancer, cervical cancer, throat cancer, oral cancer, pancreatic cancer, kidney cancer, liver cancer, lung cancer, melanoma, basal cell carcinoma, squamous cell carcinoma, head and neck cancer, stomach cancer, bone cancer, connective tissue cancer, bladder cancer, ocular cancer, nasal cancer, adipose cancer, thyroid cancer, non-Hodgkin lymphoma, small intestine cancer, Wilms tumor, gastrointestinal cancer, central nervous system (CNS) cancer, peripheral nervous system (PNS) cancer, esophageal cancer, Karposi sarcoma, gallbladder cancer, Hodgkin lymphoma, multiple myeloma, osteoscarcoma, neuroblastoma, rhabdomyoscarcoma, sinus cancer, retinoblastoma, and salivary cancer. In certain embodiments, the cancer cells are located in the subject in one or more of: the ovaries, the peritoneal cavity, peritoneal fluid, and the peritoneum. Some embodiments of methods and compositions of the invention can be used to treat a cancer or tumor that presents with a plural effusion.

A composition of TS and VitE may be utilized and administered to treat numerous different types of cells, including but not limited to: a pleural cell, a peritoneal cell, a dermal cell, a breast tissue cell, an ovarian cell, a mesothelioma cell, a muscle cell, a circulatory cell, a connective tissue cell, a bone cell, an exocrine cell, an endocrine cell, an organ cell, a mesenchyme cell, a connective tissue cell, an epithelial cell, an endothelial cell, a neuronal cell, a glial cell, a glandular cell, a stromal cell, a renal cell, a thyroid cell, a stem cell, a hematopoietic cell, a lymphoid cell, a myeloid cell, an erythroid cell, a cardiomyocyte, an hepatocyte, an astrocyte, an oligodendrocyte, and an adipocyte. In certain aspects of the invention a cell treated by a method comprising a contacting a cell with a composition comprising TS and VitE with or without contacting the cell with one or more compositions comprising one or more of GV, TLK-199, and another cancer therapeutic compound may be a cancer cell, and the cancer may be any of the aforementioned cancers or other art-known cancers or neoplasms. In some aspects of the invention the cancer is a malignant mesothelioma and in certain embodiments of the invention the cancer is an ovarian cancer.

In certain aspects of the invention a plurality of cancer cells comprises a tumor that includes cancer cells in spatial proximity to each other. In some aspects of the invention a plurality of cells may not be in spatial proximity to each other, for example they may be in a subject but may be spatially separated in two or more different spatial regions, tissues, and/or organs of the subject. In some aspects of the invention, a plurality of cancer cells comprises one or more of a primary cancer and a secondary cancer (for example a metastasis); one or more primary cancers; and/or one or more secondary cancers. As used herein a primary cancer is used in reference to the initial, originating cancer and a secondary cancer comprises cancer cells that have broken away from a primary cancer and traveled to and are present in a different tissue or organ in the subject. A cancer cell from a secondary cancer may be the same cancer type as the originating primary cancer. In certain embodiments, a subject may have more than one cancer type. In certain embodiments of the invention a cancer cell is a metastatic cancer cell.

Non-limiting examples of subjects to which methods and compositions of the present invention can be applied are subjects who have been diagnosed with, are suspected of having, or are at risk of having one or more cancers. Methods of the invention may be applied to a subject who, at the time of treatment using a method that includes administering a composition comprising TS and VitE with or without contacting the cell with one or more compositions comprising one or more of GV, TLK-199, and another cancer therapeutic compound has been diagnosed with a cancer and is (1) undergoing treatment for one or more cancers, (2) has undergone treatment for one or more cancers, and/or (3) will be administered a treatment for one or more cancers.

In some aspects of the invention, a subject is at risk of having or developing one or more cancers. In some aspects of the invention, a subject is at risk of having or developing a primary cancer. In some aspects of the invention, a subject is at risk of having or developing a secondary cancer. A subject at risk of developing a primary cancer or a secondary cancer has an increased probability of developing the cancer, compared to a control risk of developing the primary cancer or secondary cancer, respectively. In some embodiments of the invention, a level of risk may be statistically significant compared to a control level of risk. A subject at risk may include, for instance, a subject having a genetic abnormality, the presence of which has been demonstrated to have a correlative relation to a higher likelihood of developing a cancer; a subject who has undergone a treatment for a primary cancer (for example, but not intended to be limiting, removal of a primary tumor) but who considered to be at risk for a secondary cancer and/or metastasis and/or another type of cancer; a subject undergoing cancer treatment other than a cancer treatment of the invention; a subject having a family and/or personal medical history of one or more cancers; a subject exposed to agents such as asbestos, chemical toxins, or activities; and/or a subject who has previously been treated for the cancer and is in apparent remission.

The effectiveness of a treatment comprising administering a composition comprising TS and VitE to a subject with or without also administering to the subject one or more compositions comprising one or more of GV, TLK-199, and another cancer therapeutic compound can be determined and compared to control values. A control value may be a predetermined value, which can take a variety of forms. It can be a single cut-off value, such as a median or mean. It can be established based upon comparative groups, such as in groups of cells or individuals that have a cancer and are not treated with a composition comprising TS and VitE to a subject with or without also administering to the subject one or more compositions comprising one or more of GV, TLK-199, and another cancer therapeutic compound. Another comparative group may be a group of subjects with a history of a cancer and a group of subjects without such a history. The predetermined value will depend upon the particular population selected. Accordingly, the predetermined value selected may take into account the category in which an individual or cell falls. Appropriate ranges and categories can be selected with no more than routine experimentation by those of ordinary skill in the art. As used herein, "effective" and "effectiveness" means a statistically significant increase in cancer cell death when treated with a method of the invention, as compared to a control having the cancer but not treated with the composition with the same method of the invention. A level of cell death in a subject treated with a composition comprising TS and VitE with or without also administering to the subject one or more compositions comprising one or more of GV, TLK-199, and another cancer therapeutic compound using a method of the invention can be compared to a control subject not treated with the same therapeutic combination and the effectiveness means a statistically significant increase in number of cancer cells that die. In some embodiments the number of cells that die as a result of a treatment of the invention is greater than zero, and in certain embodiments of the invention the number of cells that die as a result of a treatment of the invention is more than 1, 2, 3, 4, 5, 6, 7, 8, 9, 10, 20, 30, 50, 100, 1000, 10,000 times the number of cancer cells that die in the control that is not treated with a composition comprising TS and VitE in a method of the invention.

It will be understood that controls according to the invention may be, in addition to predetermined values, samples of materials tested in parallel with the experimental materials. Examples include samples from control populations or control samples generated through manufacture to be tested in parallel with the experimental samples; and also a control may be a sample from a subject prior to, during, or after a cancer treatment, including but not limited to a treatment of the invention.

Treatment

As used herein, the terms "treat", "treated", or "treating" when used with respect to a cancer may refer to a prophylactic treatment that decreases the likelihood that a subject developing the cancer, and also may refer to a treatment after the subject has developed the cancer in order to eliminate or ameliorate the cancer, prevent the cancer from becoming more advanced (e.g., metastasizing, spreading, enlarging, etc.), and/or slow the progression of the cancer compared to progression in the absence of the therapy.

In certain embodiments of the invention, contacting a cancer cell with a composition comprising TS and VitE with or without also contacting the cancer cell with one or more of GV, TLK-199, and another cancer therapeutic compound increases the likelihood of death of the cancer cell, versus a cell not contacted with the TS and VitE composition.

Administration Strategies

A composition comprising TS and VitE may be administered alone or in combination with one or more of GV, TLK-199, another therapeutic agent, a targeting agent, and a labeling agent. Although the TS and VitE are administered in a single pharmaceutical composition the other agents such as GV, TLK-199, another cancer therapeutic compound, a targeting agent, and a labeling agent may be administered in one or more separate compositions. A composition comprising TS and VitE may be administered to a subject using single administration means or using more than one administration means depending on factors such as the location of a cancer, desired timing of administration, the status of a subject and the cancer, etc. In some aspects of the invention, a composition comprising TS and VitE is a separate composition from a composition comprising GV, TLK-199, another therapeutic agent, a targeting agent, and a labeling agent and the two or more different compositions may be administered at the same times, or may be administered sequentially, using a regimen in which their administration overlaps in part or in full. It will be understood that in some aspects of the invention two or three of TS in VitE, GV, and TLK-199 may be administered at the same time and in certain embodiments of the invention, two or three of TS in VitE, GV, and TLK-199 are in different compositions when administered. In a non-limiting example, in some embodiments of the invention, the TS in VitE and the TLK-199 are in one pharmaceutical composition and are administered to a subject together, and the GV is in a different pharmaceutical composition that is delivered either at the same time as, or at a different time than the TS in VitE and the TLK-199 are administered to the subject. The synergistic effect of administering TS in VitE, GV, and TLK-199 need not require their administration in a single composition. In another non-limiting example, TS in VitE and TLK-199 are provided in the same pharmaceutical composition and are administered together to a subject and GV is not administered to the subject as part of the treatment.

In some embodiments of treatment methods of the invention TS in VitE is administered to a subject with a cancer who is also administered one or more other therapeutic agents and treatments. Thus, for example, administration of TS in VitE may be undertaken in conjunction with chemotherapeutic agent and may enhance the cancer cell killing efficacy of the chemotherapeutic agent. A non-limiting example of a chemotherapeutic agent is: a taxane, an anthracyclines, a platinum-based drug, an anti-metabolite, a base analog, a nucleoside analogue, a nucleotide analogue, an antifolate, methotrexate, an alkaloid, vincristine, vinblastine, irinotecan, etoposide, velcade, a tyrosine kinase inhibitor, a serine/threonine kinase inhibitor, bleomycin, cyclophosphamide, cytoxan, everolimus, and metformin. In certain aspects of the invention, the TS in VitE in methods and compositions of the invention are provided in conjunction with other molecules such as targeting agents and labeling agents and used in treatment methods of the invention. A targeting agent or labeling agent may be attached to TS, GV, TLK-199 or another cancer therapeutic compound and included in a treatment method of the invention using art-known means such as, but not limited to via a covalent bond. In some aspects of the invention a targeting or labeling agent may be incorporated into TS when it is produced or may be added post-production using routine chemical manufacturing methods.

Targeting agents useful in some aspects of the invention are targeting agents that direct or assist in directing TS in VitE, and in certain embodiments of the invention one or more of GV, TLK-199, and another cancer therapeutic compound to a specific cell to be treated such as a dermal cell, ovary tissue cell, a plural cell, a peritoneal cell, a breast tissue cell, a muscle cell, a stem cell, a circulatory cell, a connective tissue cell, a bone cell, an exocrine cell, an endocrine cell, an organ cell, a mesenchyme cell, a connective tissue cell, an epithelial cell, an endothelial cell, a neuronal cell, a glial cell, a glandular cell, a stromal cell, a renal cell, a thyroid cell, a stem cell, a hematopoietic cell, a lymphoid cell, a myeloid cell, an erythroid cell, a cardiomyocyte, an hepatocyte, an astrocyte, an oligodendrocyte, an oocyte, or an adipocyte. Certain targeting agents useful in some aspects of the invention may be agents that direct or assist in directing a compound such as TS, GV, TLK-199, or another cancer therapeutic compound to an organelle such as a mitochondrion.

A targeting agent of choice will depend upon the nature of the cancer. In some instances it may be desirable to target the combination of agents to one or more pleural regions, lung cells, peritoneal regions, peritoneal cells, dermal cells, breast tissue cells, muscle cells, circulatory cells, connective tissue cells, stem cells, bone cells, exocrine cells, endocrine cells, organ cell, mesenchyme cells, connective tissue cells, epithelial cells, endothelial cells, neuronal cells, glial cells, glandular cells, stromal cells, renal cells, thyroid cells, stem cells, hematopoietic cells, lymphoid cells, myeloid cells, erythroid cells, cardiomyocytes, hepatocytes, astrocytes, oligodendrocytes, oocytes, and adipocytes. Those of ordinary skill in the art will be aware of and will be able to select and use suitable targeting agents in embodiments of the invention using routine methods. A non-limiting example of a targeting agent useful in certain embodiments of the invention is a cell-penetrating peptide, a cell internalization agent, sequence, a small molecule, a polynucleotide, a liposome, a PEGylated liposome, an aquasome, a biodegradable polymer, a nanoparticle, an oligonucleotide, and other targeting polypeptides.

The invention in some aspects includes an agent that targets one or more of TS, GV, TLK-199, and another cancer therapeutic compound to mitochondria. In some embodiments of the invention the TS that is in VitE is in association with (for example: is attached to) a mitochondrial-targeting agent. A non-limiting example of a mitochondrial targeting agent is a Gramicidin S based mitochondrial targeting agent, a mitochondria-targeting peptide; a nanoparticle that traffics to mitochondria, and a liposome-based delivery systems for mitochondria, an agent utilizing the carnitine-acylcarnitine translocase system, cytochromes, and malate dehydrogenase. A non-limiting example of a mitochondrial targeting agent that may be used in methods of the invention to target one, two, or three of TS, GV, TLK-199, and another cancer therapeutic compound to mitochondria of a cell is Triphenylphosphonium (TPP). Additional examples of targeting signals that may be used in some embodiments of the invention are set forth in Diekert, K., et al., PNAS (1999) vol 96, No. 21, 11752-11757; Murphy, M. Biochimica et Biophysica Acta 1777 (2008) 1028-1031; Addya, S., et al., J. Cell Biology, (1997) Vol. 139, No. 3, 589-599; Del Gaizo, V., et al., (2003) Mol. Gen. and Metabol., Vol. 80, 170-180, which are incorporated herein by reference.

Labeling agents may be used in certain embodiments of methods, compounds, and compositions of the invention to determine the location of one or more of: TS, GV, TLK-199, and other cancer therapeutic compounds in cells and tissues administered using an embodiment of a method of the invention and also may be used to assess the cell, tissue, or organelle location of treatment compounds that have been administered. Procedures for attaching and utilizing labeling agents such as enzymatic labels, dyes, radiolabels, fluorescent labels, etc. are well known in the art.

Compositions, compounds, and methods of the invention may be enhanced by utilization in combination with other procedures for treating a cancer. In some instances a treatment procedure may involve administration of another therapeutic agent or treatment such a medicament and/or surgery, radiation therapy, etc. Thus, in some embodiments of the invention, administration of a composition comprising TS and VitE is performed at one of more of: prior to, coincident with, or after administration of another therapy for treating the cancer. Treatment methods of the invention that include administration of a composition comprising TS and VitE can be used at any stages of a cancer including in a pre-cancer, dysplasia, tumor, metastasis, remission, relapse, etc. Methods of the invention may also be used for subjects who have previously been treated with one or more other anti-cancer medicament, chemotherapeutic, surgery, or radiation methods that were not successful, were minimally successful, and/or are no longer successful at slowing or stopping progression of the cancer in the subject.

Effective Amounts

TS and VitE are administered to a cell or subject in an effective amount for treating a cancer. An "effective amount for treating a cancer" is an amount necessary or sufficient to realize a desired biologic effect. For example, an effective amount of TS and VitE in a method of the invention is that amount necessary to do one or more of (i) slowing or halting progression of the cancer; (ii) killing a plurality of cancer cells, and (iii) reversing one or more symptoms of the cancer. According to some aspects of the invention, an effective amount is that amount of TS in VitE, either alone or in combination with another medicament or treatment for a cancer that when administered results in a desired therapeutic response in the subject, including one or more of: prevention of the cancer, prevention of a metastasis of the cancer, and treatment of the cancer. In some aspects of the invention, a desired biological effect may be one or more of: death of a plurality of cancer cells; the amelioration and or absolute elimination of symptoms resulting from the cancer; a partial or complete abrogation of the cancer, as evidenced for example, by a diagnostic test that indicates the subject is free of the cancer, or that one or more of the presence, level, or tumor size, metastasis, and severity of the cancer is reduced.

Typically an effective amount of TS in VitE will be determined in clinical trials, establishing an effective dose for a test population versus a control population in a blind study. In some embodiments, an effective amount will be that results in a desired response, e.g., an amount that diminishes a cancer; maintains a cancer in remission in cells and/or a subject with the cancer. Thus, an effective amount to treat a cancer may be the amount that when administered increases cell death of a plurality of cancer cells in the subject to a level that is higher than the level of cancer cell death that would occur in the subject or tissue without the administration of the TS in VitE. In the case of treating a cancer a desired response to a treatment of the invention may be reducing or eliminating one or more symptoms or physiological characteristics of the cancer in a cell, tissue, and/or subject. The reduction or elimination may be temporary or may be permanent. The status of the cancer can be monitored using art-known methods. In some aspects of the invention, a desired response to treatment of a cancer may comprise delaying or preventing onset of the cancer, slowing, delaying, or stopping a cancer's progression, maintaining remission of a cancer, etc.

An effective amount of TS administered in solution with VitE in a treatment method of the invention may also be determined by assessing physiological effects of administration of the TS in VitE on a cell or subject, such as a an increase in cancer cell death, a decrease of the cancer, etc. following administration. As herein the terms "administrating" and "administering" when used in reference to treating one or more cancer cells means contacting the one or more cancer cells with TS that is in solution with a VitE compound. In some embodiments of a treatment method of the invention also comprises administering one or more of: GV, TLK-199, and another cancer therapeutic compound to the subject to whom the TS in VitE is administered. In certain embodiments of the invention, one or more of TS, GV, TLK-199, and another cancer therapeutic compound are part of a pharmaceutical composition. In certain embodiments of the invention the TS in VitE is part of a pharmaceutical composition. In certain embodiments of the invention, a composition comprising TS in VitE and one or more compositions that include one or more of GV, TLK-199, and another cancer therapeutic agent may be administered as part of one, two, or three different pharmaceutical compositions, wherein the manner of administration of each of the compositions is suitable to contact one or more cancer cells with the TS, GV, TLK-199 and/or other cancer therapeutic compound. Some embodiments of pharmaceutical compositions of the invention also include a pharmaceutically acceptable carrier. It will be understood that if one or more of TS, GV, TLK-199, and another cancer therapeutic compound are part of separate pharmaceutical compositions, each of the pharmaceutical compositions, can but need not include the same pharmaceutically acceptable carrier.

Assays suitable to determine efficacy of TS in VitE and/or a combination of TS in VitE with one or more of GV, TLK-199, and another cancer therapeutic agent will be known to those skilled in the art and can be employed for measuring the level of the response to a treatment and an amount and dosage of the combination of the compounds administered to a subject. The amount of TS in VitE, as well as the amounts of one or more of GV, TLK-199, and another cancer therapeutic agent can be modified based, at least in part, on such measurements. Non-limiting examples of measurements of response to a cancer treatment of the invention include cancer diagnostic testing, staging, tumor measure, scans, etc. The amount of a treatment may be varied for example by one or more of: increasing or decreasing the amount of a pharmaceutical composition administered, changing the pharmaceutical composition administered, changing the route of administration, changing the dosage timing, changing administration of another therapeutic agent, a non-limiting example of which is a chemotherapeutic agent, and so on. The effective amount will vary with the particular cancer being treated, the age and physical condition of the subject being treated; the stage and severity of the cancer, the duration of the treatment, the nature of a prior, concurrent, or impending therapy (if any), the specific route of administration, and additional factors within the knowledge and expertise of the health practitioner. For example, though not intended to be limiting, an effective amount of TS may depend on the manner with which it is delivered, as well as whether or not GV or TLK-199 are also included in the pharmaceutical composition that includes the TS in VitE. It will be understood that in some aspects of the invention, a cancer therapeutic method may include one or more administrations of TS in VitE to a subject and that the subject may, but need not be administered one or more additional compositions comprising TS that is not in VitE.

An effective amount of TS in VitE, with or without administration of one or more of GV, TLK-199, and another cancer therapeutic compound for treatment of a cancer may vary depending upon the specific compounds included, the mode of delivery of the compounds, and whether the treatment is used alone or in combination with another therapeutic agent or compound. The effective amount for any particular application can also vary depending on such factors as the cancer being treated, the particular compound being administered, the size of the subject, or the severity of the cancer. A skilled artisan can empirically determine the effective amount of a particular compound of the invention without necessitating undue experimentation. Combined with the teachings provided herein, one skilled in the art able to choose to administer TS in VitE with or without one or more of GV, TLK-199, and another cancer therapeutic compound, taking into account factors such as compound potency, relative bioavailability, patient body weight, severity of adverse side-effects and preferred mode of administration, to plan and utilize an effective prophylactic or therapeutic treatment regimen that does not cause substantial undesirable toxicity in a treated subject and is effective to treat a cancer in the subject.

A pharmaceutical composition dosage and/or dosage of TS in VitE and/or one or more of GV, TLK-199, and another cancer therapeutic compound can be adjusted by an individual health care provider or veterinarian, particularly in the event of any complication.

In some embodiments, the quantity of Vitamin E-TPGS administered to a subject in a single dose is no more than 30 g. In some embodiments the Vitamin E-TPGS is administered in 1, 2, 3, 4, 5, or more doses per a 24 hour period. In some embodiments, the quantity of GV administered in a 24 hour period ranges from 10 ng to 200 mg. In some embodiments the amount of one or more of TS, Vitamin E-TPGS, and GV are each independently selected within and between each of one or more 24 hour periods. In certain embodiments, the contacting includes contacting with one or more compositions that include TS and Vitamin E-TPGS. In certain embodiments, the contacting includes contacting with one or more compositions that include TS and Vitamin E-TPGS. In certain embodiments, the contacting includes contacting with one or more compositions that include TS and Vitamin E-TPGS. In some embodiments, the method also includes contacting with a composition comprising GV. In some embodiments, the molar concentration of the TS in the composition is in a range from 10 nM to 5000 μM. In certain embodiments, the molar concentration of the GV in the composition is in a range from 10 nM to 10 mM. In some embodiments, the molar concentration of the Vitamin E-TPGS in the composition is in a range from 10 nM to 145 mM. In some embodiments, the molar concentration of the Vitamin E-TPGS in the composition is in a range from 10 nM to 132 mM. In some embodiments, the molar concentration of the Vitamin E-TPGS in the composition is at least 10 nM, 50 nM, 100 nM, 1000 nM, 10,000 nM, 1 mM, 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, or 160 mM. For use in a combination treatment method of the invention, a therapeutically effective amount of each of TS in VitE, GV, TLK-199, and/or another cancer therapeutic agent are independently determined and typically vary from 0.01 mg/kg to about 1.0 g/kg, from about 0.1 mg/kg to about 500 mg/kg, or from about 0.2 mg/kg to about 100 mg/kg, in one or more dose administrations daily, for one or more days.

In some embodiments, the quantity of TS administered in a 24 hour period ranges from 10 ng to 1 g. In some embodiments, the quantity of Vitamin E-TPGS administered in a 24 hour period ranges from 10 ng to 500 g. In some embodiments, the quantity of Vitamin E-TPGS administered to a subject in a single dose is no more than 30 g. In some embodiments the Vitamin E-TPGS is administered in 1, 2, 3, 4, 5, or more doses per a 24 hour period. In some embodiments, the quantity of GV administered in a 24 hour period ranges from 10 ng to 200 mg. In some embodiments the amount of one or more of TS, Vitamin E-TPGS, and GV are each independently selected within and between each of one or more 24 hour periods.

In certain embodiments, the contacting includes contacting with one or more compositions that include TS and Vitamin E-TPGS. In certain embodiments, the contacting includes contacting with one or more compositions that include TS and Vitamin E-TPGS. In certain embodiments, the contacting includes contacting with one or more compositions that include TS and Vitamin E-TPGS. In some embodiments, the method also includes contacting with a composition comprising GV. In some embodiments, the molar concentration of the TS in the composition is in a range from 10 nM to 5000 μM. In certain embodiments, the molar concentration of the GV in the composition is in a range from 10 nM to 10 mM. In some embodiments, the molar concentration of the Vitamin E-TPGS in the composition is in a range from 10 nM to 132 mM. In some embodiments, the molar concentration of the Vitamin E-TPGS in the composition is at least 10 nM, 100 nM, 1000 nM, 10,000 nM, 1 mM, 10 mM, 50 mM, 60 mM, 70 mM, 80 mM, 90 mM, 100 mM, 110 mM, 120 mM, 130 mM, 140 mM, 150 mM, or 160 mM. In some embodiments, the one or more compositions further include one or more of a pharmaceutically acceptable carrier and excipient.

The absolute amount administered will depend upon a variety of factors including a concurrent treatment, the number of doses and the individual subject parameters including age, physical condition, size and weight. These are factors well known to those of ordinary skill in the art and can be addressed with no more than routine experimentation. In some embodiments, a maximum dose can be used, that is, the highest safe dose according to sound medical judgment. Depending on the route of drug delivery (direct administration vs. systemic) the concentration of drug for clinical administration will vary. In certain embodiments of the invention, the percentage of VitE-TPGS in a compositions comprising solubilized TS in VitE-TPGS can be up to 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, including all percentages within the range provided. In some aspects of the invention, a composition administered to a subject for treating a cancer comprises 5% VitE-TPGS solubilized TS. In some embodiments of methods of the invention dimethyl sulfoxide (DMSO) is also included in one or more compositions administered to a subject.

Multiple doses of TS in VitE are also contemplated. In some instances, TS in VitE is administered to a subject once, twice, three or more times, at least daily, every other day, weekly, every other week, monthly, etc. Doses may be administered once per day or more than once per day, for example, 2, 3, or more times in one 24 hour period. In some embodiments of the invention, a composition comprising TS and VitE is administered to a subject zero, one, or more times daily for 1, 2, 3, 4, 5, 6, 7 days in a week. As a non-limiting example, a composition of the invention comprising TS and VitE may be administered once on day 1, zero times on day 2, twice on day 3, zero times on days 4 and 5, and once on days 6 and 7 in a week. The administration schedule can be determined based on the need of a subject. In some embodiments of the invention a composition comprising TS and VitE is administered to a subject for at least 1, 2, 3, 4, 5, 6, 7, 8, 9, 10, 15, 20, 25, 30, 35, 40, or more weeks, at a frequency of one or more times in one or more days of one or more of the weeks. A schedule of administration of a composition of the invention comprising TS and VitE can be include a regular or irregular administration frequency and the frequency can be determined based on parameters such as but not limited to: the severity of the condition, etc.

Pharmaceutical compositions of the invention may be administered alone, in combination with each other, and/or in combination with other drug therapies, or other treatment regimens that are administered to subjects with a cancer. Pharmaceutical compositions used in the embodiments of the invention preferably are sterile and contain an effective amount of a combination of TS in VitE to do one or more of: kill a contacted cancer cell and produce the desired therapeutic response in a unit of weight or volume suitable for administration to a subject.

The dosing of a pharmaceutical composition comprising TS and VitE that is administered to a subject can be chosen in accordance with different parameters, in particular in accordance with the mode of administration used and the state of the subject. Other factors may include the desired period of treatment. In the event that a response in a subject is insufficient at the initial doses applied, higher doses (or effectively higher doses by a different, more localized delivery route) may be employed to the extent that patient tolerance permits.

Administration Methods

A variety of administration routes for TS in VitE are available. The particular delivery mode selected will depend upon the particular condition being treated and the dosage required for therapeutic efficacy. Methods of this invention, generally speaking, may be practiced using any mode of administration that is medically acceptable, meaning any mode that produces effective levels of treatment without causing clinically unacceptable adverse effects. In some embodiments of the invention, a composition of TS in VitE is administered via an oral, enteral, mucosal, percutaneous, and/or parenteral route. The term "parenteral" includes subcutaneous, intravenous, intramuscular, intrapleural, intraperitoneal, and intrasternal injection, or infusion techniques. Other routes include but are not limited to nasal (e.g., via a gastro-nasal tube), dermal, vaginal, rectal, and sublingual. Delivery routes of the invention may include intrathecal, intraventricular, or intracranial.

In some embodiments of methods of the invention a means of administering a composition comprising TS in VitE to cells and/or a subject comprises using a catheter to infuse the composition into a body cavity of a subject and/or to wash a body cavity of a subject with the composition. Examples of catheters that may be used in certain embodiments of the invention include, but are not limited to, an intra-pleural catheter and an intra-peritoneal catheter. In a non-limiting example, an intra-pleural catheter is used to administer one or more doses of a composition of the invention comprising TS in VitE into the plural cavity a subject with a plural effusion. In another non-limiting example, a subject with ovarian cancer may be administered a composition of the invention comprising TS in VitE to the peritoneal cavity using an intra-peritoneal catheter.

In some embodiments of the invention, a composition comprising TS and VitE, or one or more compositions comprising GV, TLK-199, and/or another cancer therapeutic compound may be placed within a slow release matrix and administered by placement of the matrix in the subject. In some aspects of the invention, one or more of TS in VitE, GV, TLK-199, and another cancer therapeutic agent may be administered to a cell and/or subject using nanoparticles coated with a delivery agent that targets a specific cell or organelle, a non-limiting example of which is a mitochondrion.

One or more of TS in VitE, GV, TLK-199, and another cancer therapeutic compound may be administered in formulations, which may be administered in pharmaceutically acceptable solutions, which may routinely contain pharmaceutically acceptable concentrations of salt, buffering agents, preservatives, compatible carriers, adjuvants, and optionally other therapeutic ingredients. According to methods of the invention, one or more of the TS in VitE, GV, TLK-199, and other cancer therapeutic compounds may be administered in one or more pharmaceutical compositions. In general, a pharmaceutical composition comprises the compound of the invention and a pharmaceutically-acceptable carrier. Pharmaceutically acceptable carriers are well known to the skilled artisan and may be independently selected and utilized using routine methods. As used herein, a pharmaceutically-acceptable carrier means a non-toxic material that does not interfere with the effectiveness of the biological activity of the active ingredients, e.g., the ability of TS in VitE to kill a cancer cell.

Pharmaceutically acceptable carriers may include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

In some embodiments of the invention, one or more of: TS in VitE, GV, TLK-199, and another cancer therapeutic compound is administered directly to a tissue. In some embodiments, the tissue to which the compound is administered is a tissue in which cancer is present or is likely to be present or to arise. Direct tissue administration may be achieved by washing a tissue in a subject with a solution that includes TS in VitE. Such a solution may, but need not also include one or more of GV, TLK-199 and another cancer therapeutic compound. Administration using a washing means may also be referred to as: lavage and may include delivering TS in VitE to a subject by flowing a solution that contains the TS in VitE into a subject in a manner that the solution contacts cancer cells in the subject. The contact between a subject's tissues and the TS in VitE may be maintained for a period of time, such as for at least 0.1, 0.5, 1, 2, 3, 4, 5, 6, 7, 8, 9, 10, 15, 20, 25, 30, 35, 40, 45, 50, 55, 60, 65, 70, 75, 80, 85, 90, 120, 180, 240, 300, 360, 420, or more minutes, including each integer within the listed range of times. Contacting a cancer cell with TS in VitE may also be achieved using direct injection of a composition comprising TS in VitE, or other art-known means. In some embodiments of the invention treatment methods comprise administering a composition comprising TS in VitE to a subject using an intra-plural wash. It will be understood that a combination treatment of the invention may include contacting cells in a subject with TS in VitE and also contact cells in the subject with one or more of GV, TLK-199, and another cancer therapeutic compound using a washing means and contacting cells in the subject with another of TS in VitE, GV, TLK-199 or another cancer therapeutic compound using a different means, non-limiting examples of which are: IV administration, slow release administration, etc. A composition comprising TS in VitE may be administered once, or alternatively may be administered in a plurality of administrations. If administered once or multiple times, the TS in VitE may be administered by the same route each time or using one or more different administration routes. For example, the first (or the first few) administrations may be made directly into the affected tissue while later administrations may be systemic.

In embodiments of the invention in which TS in VitE is to be administered systemically, the TS in VitE composition may be formulated for parenteral administration by injection, e.g., by bolus injection or continuous infusion. Formulations for injection may be presented in unit dosage form, e.g., in ampoules or in multi-dose containers, with or without an added preservative. The pharmaceutical compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day may be used as needed to achieve appropriate systemic or local levels of TS in VitE.

In some embodiments of the invention nanoparticles may be used in administration of a composition of the invention such as a composition comprising TS in VitE, and/or a composition comprising one or more of GV, TLK-199, and another cancer therapeutic compound. Methods for using nanoparticles for drug delivery are known in the art, for example see: Choi, Y. H. and Han, H. J. Pharm. Invest. (2018) 48:43-60; Onoue, S., et al., (2014) Int. J. Nanomed. 9: 1025-1037; and Schroeder, A. et al., (2011) Nat. Rev. Cancer, December 23:12(1)39-50, each of which is incorporated herein by reference.

In yet other embodiments, a delivery vehicle is a biocompatible microparticle or implant that is suitable for implantation into the mammalian recipient. Exemplary bioerodible implants that are useful in accordance with this method are described in numerous publications, see for example, Song, R. et al., Drug Design, Development and Therapy 2018:12 3117-3145; Ulery, B., et al. J Polym Sci B Polym Phys. 2011 Jun. 15; 49(12): 832-864; each of which is incorporated by reference herein), which describe biocompatible, biodegradable polymeric matrix for administering pharmaceutical compounds. Such delivery means are well known in the art and can be used to achieve sustained release of a compound of the invention in a subject, and may be selected not to degrade, but rather, to release by diffusion over an extended period of time.

Both non-biodegradable and biodegradable polymeric matrices can be used to deliver a therapeutic compound of the invention, including but not limited to: TS in VitE, GV, TLK-199, or another cancer therapeutic compound to a cell and/or subject. In some embodiments, a matrix may be biodegradable. Matrix polymers may be natural or synthetic polymers. A polymer can be selected based on the period of time over which release is desired, generally in the order of a few hours to a year or longer. Typically, release over a period ranging from between a few hours and three to twelve months can be used. The polymer optionally is in the form of a hydrogel that can absorb up to about 90% of its weight in water and further, optionally is cross-linked with multivalent ions or other polymers.

In certain embodiments of the invention, TS in VitE and/or one or more of GV, TLK-199, or another cancer therapeutic compound may be delivered using a bioerodible implant by way of diffusion, or by degradation of the polymeric matrix. Exemplary synthetic polymers for such use are well known in the art. Biodegradable polymers and non-biodegradable polymers can be used for delivery of a therapeutic compound used in a method of the invention using art-known methods. Bioadhesive polymers such as bioerodible hydrogels may also be used to deliver one or more of TS in VitE, GV, TLK-199, and/or another cancer therapeutic compound for an embodiment of a cancer treatment method of the invention. Additional suitable delivery systems can include time-release, delayed release or sustained-release delivery systems. Such systems can avoid repeated administrations of one or more TS in VitE, GV, TLK-199, and another cancer therapeutic agent, which increases convenience to the subject and the health care provider. Many types of release delivery systems are available and well known to those of ordinary skill in the art. In addition, pump-based hardware delivery systems can be used, some of which are adapted for implantation.

Use of a long-term sustained release implant may be particularly suitable for prophylactic treatment of subjects and for subjects at risk of developing a recurrent cancer. Long-term release, as used herein, means that the implant is constructed and arranged to delivery therapeutic levels of the active ingredient for at least 30 days, 60 days, 90 days or longer. Long-term sustained release implants are well-known to those of ordinary skill in the art and include some of the release systems described above.

Therapeutic formulations for use in embodiments of therapeutic methods of the invention may be prepared for storage by mixing the TS, GV, and/or TLK-199 compounds having the desired degree of purity with optional pharmaceutically acceptable carriers, excipients or stabilizers [Remington's Pharmaceutical Sciences 21$^{st}$ edition, (2006)], in the form of lyophilized formulations or aqueous solutions. Acceptable carriers, excipients, or stabilizers are nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG). Non-limiting examples of formulations for delivery of one or more cancer therapeutic compounds in one embodiment of a method of the invention include but are not limited to one or more of: TS, GV, TLK-199, VitE-TPGS, DMSO, normal saline, Kolliphor-EL, dextrose, and sodium chloride.

Efficacy Determination and Assays

Certain aspects of the invention include methods to assess the efficacy of TS in solution with VitE in treatment of a cancer. Such methods may include comparing the effect on a cancer test cell contacted with the TS in VitE to the status of a substantially similar cancer control cell that is not contacted with the TS in VitE. A change in one or more of desirable effects such as, but not limited to: increased likelihood of cancer cell death indicates effectiveness of the TS in VitE for treatment of cancer. In some embodiments of the invention, assay methods may include obtaining a biological sample from a subject, contacting the sample with TS in VitE and assessing the cell's response (e.g., increased likelihood of cell death, etc.). The test cell's response may be compared to a control cancer cell. As used herein a biological sample may be an in vitro biological sample, or may a sample that is detected (e.g., obtained) in vivo. As used herein, a biological sample may be a cell sample, tissue sample, blood sample, bodily fluid sample, subcellular sample, etc. A biological sample may include cells, tissues, or organelles and may include cells such as but not limited to: dermal cells, cells from a plural space, cells from peritoneal space, ovary tissue cells, breast tissue cells, muscle cells, circulatory cells, connective tissue cells, stem cells, bone cells, exocrine cells, endocrine cells, organ cell, mesenchyme cells, connective tissue cells, epithelial cells, endothelial cells, neuronal cells, glial cells, glandular cells, stromal cells, renal cells, thyroid cells, stem cells, hematopoietic cells, lymphoid cells, myeloid cells, erythroid cells, cardiomyocytes, hepatocytes, astrocytes, oligodendrocytes, oocytes, and adipocytes. In some embodiments of the invention, a biological sample may comprise one or more cancer cells.

Assays to assess a cancer may include but are not limited to (1) characterizing the efficacy of a treatment comprising administering TS in VitE in treating a cancer in a subject; (2) evaluating a combination treatment that comprises administering TS in VitE and administering one or more compounds, chemotherapeutic agents, radiation treatments, surgical treatments, and other treatments, (3) selecting a treatment for a cancer based at least in part on the determined efficacy of the TS in VitE; and (4) administering TS in VitE to a subject as at least a portion of a treatment of a cancer in the subject. Thus, subjects can be characterized, treatment regimens can be monitored, treatments can be selected and diseases status can be better understood using embodiments of methods of the present invention.

The invention, in some aspects, includes various assays to determine the efficacy of a treatment comprising administering a composition comprising TS in VitE to a cancer cell and/or subject. Methods of the invention that are useful to determine efficacy of a treatment method of the invention in cells, tissues, subjects, and samples (e.g., from subjects, in culture, etc.), include, but are not limited to: diagnostic assays to determine cancer cell death, etc. Assessments of efficacy of TS in VitE to treat a cancer can be done in vitro, for example in cell culture, cell samples, cell suspensions, etc. or can be done in vivo, for example in a living subject using art-known cancer diagnostic assessments and tracking methods.

As will be appreciated by those of ordinary skill in the art, the evaluation of a treatment also may be based upon an evaluation of the symptoms or clinical end-points of a cancer and such evaluations can be used in conjunction with methods of the invention to assess the status of a cancer and/or the efficacy of a treatment of the invention for a cancer.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Studies were performed to test the effects on cell viability of mesothelial (LP9) and malignant mesothelioma (HM) cells in culture when contacted with thiostrepton (TS) or TS diluted in Vitamin E-TPGS (VitE-TPGS, D-alpha-tocopherol polyethylene glycol 1000 succinate).

Thiostrepton is poorly soluble in aqueous solution and therefore limits clinical use of the compound. Studies were performed to determine the ability of a number of different solutions to solubilize TS (see Example 4). Results indicated that a solution of 5% VitE-TPGS solubilized TS to millimolar concentrations and this solution was used in further studies to determine whether TS activity was retained in cell culture using this formulation.

Methods

Figure 2A:
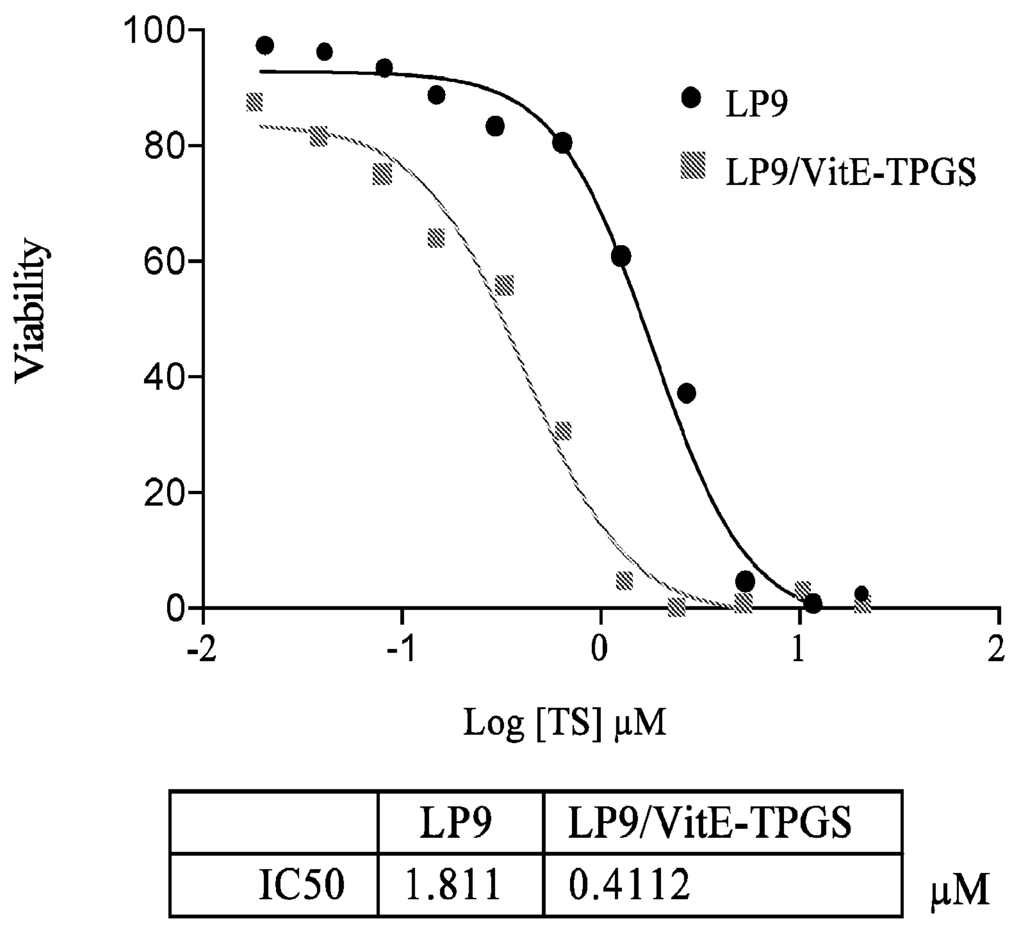
FIG. 2A-B provides graphs showing sensitivity of LP9 cells (FIG. 2A) and HM cells (FIG. 2B) treated with TS or TS diluted in 5% VitE (33 mM)-TPGS/0.9% NaCl. IC50s were calculated for TS alone or in combination with VitE-TPGS. Graphs show viability versus Log [TS] μM.
Figure 2B:
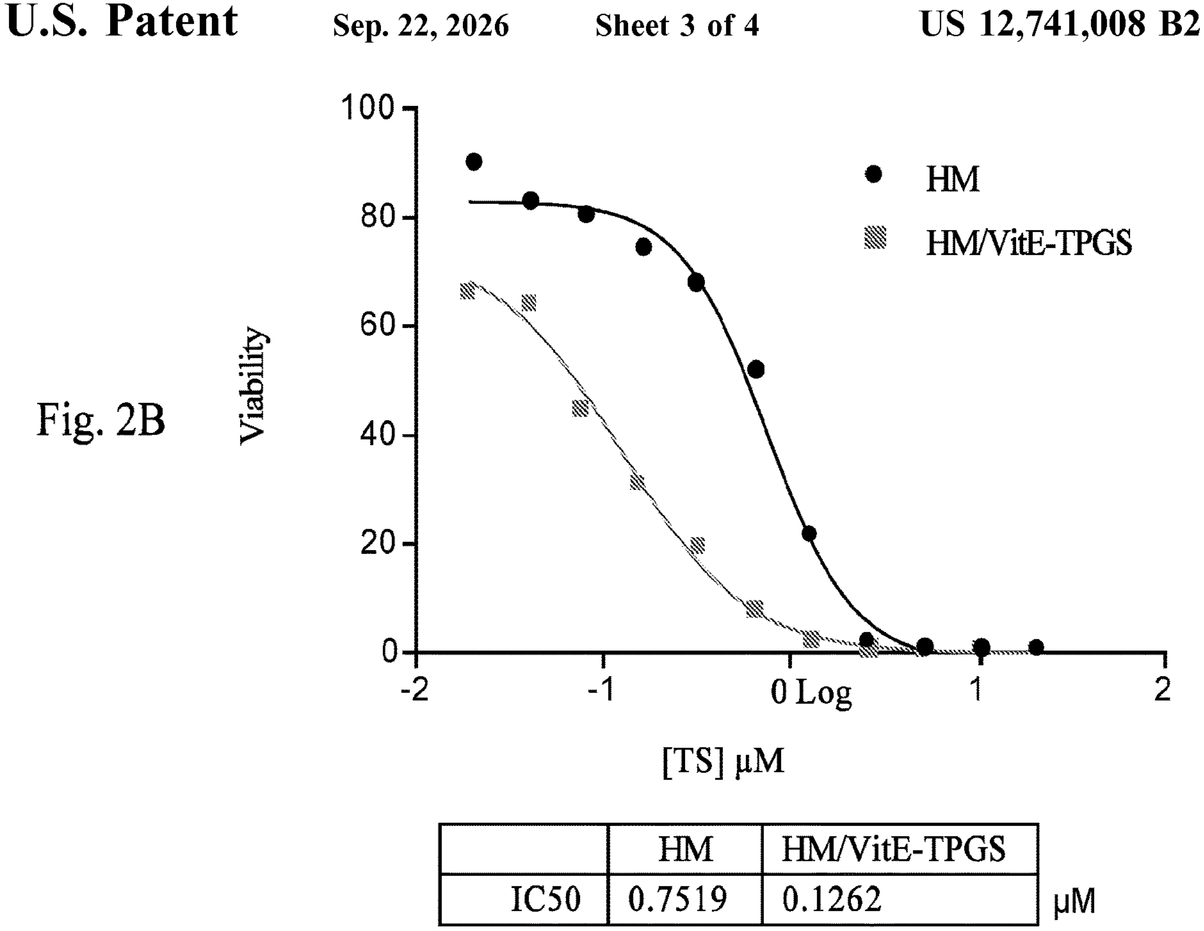

Indicated cell lines were plated into 96 well plates and allowed to adhere overnight. The following day test compounds were serially diluted in duplicate wells onto cells in complete tissue culture media. VitE-TPGS was serially diluted from a starting concentration of 0.025% (w/v) in 0.9% NaCl and added to LP9 or HM cells (FIG. 1). TS, dissolved in DMSO, was diluted to a starting concentration of 20 μM into cell culture media and serially diluted or diluted from a 1.5 mM TS/DMSO/5% VitE-TPGS (33 mM)/0.9% NaCl solution to a starting concentration of 20 μM TS/0.06% VitE-TPGS and serially diluted onto LP9 or HM cells (FIG. 2). Cells were incubated with test compounds for 48 hours before determining cell number using an indirect readout of cell viability by staining residual cells with crystal violet. The inhibitory concentration (IC50) in which 50% of the cells are not viable, was determined for tested compounds.

Results

VitE-TPGS was determined to be cytotoxic to both normal mesothelial (LP9) and malignant mesothelioma (HM) cells (FIG. 1). HM cells showed increased cytotoxicity to VitE-TPGS compared to LP9 mesothelial cells (IC50 for LP9 0.0014% vs. 0.0006% for HM cells). TS diluted in VitE-TPGS was more cytotoxic to LP9 and HM cells compared to TS alone (FIG. 2). Additionally, HM cells were more sensitive to TS than LP9 cells, a therapeutic window that was consistently observe to be maintained when TS was combined with VitE-TPGS in either cell line.

Example 2

The studies outlined in Example 1 are also carried out in additional cell lines. The results support the results seen in Example 1.

Example 3

Mouse experiments are performed to test the effects on malignant mesothelioma (MM) cells and tumor growth in vivo, by contacting the in vivo MM cells with combinations of TS and VitE-TPGS.

Example 4

This study was performed to determine the intrinsic solubility of the test article in a variety of formulation systems as detailed below. In testing described, the test article was Thiostrepton (TS).

Methods

This method measured equilibrium solubility after 24 h incubation with the desired formulation mixture. The solubility of the test article in each formulation mixture was measured by comparison of the AUC of the LC/MS spectrum obtained by injection of the solution of the test article in the desired solvent to the AUC of a reference standard solution. Studies were performed with TS as the test article, also referred to as the active pharmaceutical ingredient (API). The reference solution was made fresh for every time point. Data was then calculated to give % test article remaining as function of time. The procedure method was as follows:

1) A stock solution of the active pharmaceutical ingredient (API) was prepared in a 1,4-dioxane at 10 mM.
2) Nineteen 200 μl portions of stock were dispensed into 19 clean 500 μl micro-centrifuge tubes and the solvent removed by a stream of nitrogen. The 19 tubes were marked with numbers 1-19.
3) Five 200 μl portions of stock were dispensed into 5 clean 200 μl micro-centrifuge tubes and the solvent removed by a stream of nitrogen; these tubes were marked: S1, S2, S3, S4 and S5 and were to be saved for quantization by LC/MS.
4) The vehicles were prepared on a w/w basis for co-solvents, and on a molar basis for salts.
5) 200 μL of each vehicle was introduced into the appropriate micro centrifuge tube 1-19, corresponding to that vehicle. The final concentration of API was 10 mM. These were the test samples.
6) The sample tubes 1-19 were sonicated for 30 min and then agitated for 24h.
7) The vessel was centrifuged and 50 μl of the supernatant was removed and diluted with 350 μl of acetonitrile for LC/MS analysis. These were the test samples.

8) Micro-centrifuge tubes S1-S5 were reconstituted immediately before analysis by adding 200 μl of acetonitrile and 200 μl od 1,4-dioxane to the tubes and sonicating for 30 min. These were the standards.
9) Before analysis all 24 tubes were centrifuged.
10) 50 μl of the clear supernatant from Sample tubes 1-19 was removed and diluted into 350 μl of acetonitrile for LC/MS analysis.
11) 100 μl of the clear supernatant from Standard tubes S1-S5 was removed and diluted into 300 μl of acetonitrile for LC/MS analysis.
12) LC was run according to the following set up:

| | | | |
|---|---|---|---|
| a) Blank | b) Standard 1 | c) Samples 1-5 | d) Standard 2 |
| e) Samples 6-10 | f) Standard 3 | g) Samples 11-15 | h) Standard 4 |
| i) Samples 16-19 | j) Standard 5 | | |

13) Quantization was based on comparison to the AUC from the stock solution and was relative.

Results

The standards were run on LC/MS and the UV spectra at 254 nm, the Evaporative Light Scattering (ELSD), and the extracted ion chromatogram for the parent peak (457, M+H) were integrated to give the AUC for each time point. A freshly prepared standard was used for each time point. Using this data, the % of test article remaining was calculated (shown in Table 1).

TABLE 1

Calculated intrinsic solubility in mM of the test article in various formulations.

| Sample Number | Name | Amount of excipient in normal saline | Intrinsic solubility (mM) | CAS |
|---|---|---|---|---|
| 1 | Polyacrylic acid 450,000 amw | 1% | 0.13 | 9003-01-4 |
| 2 | Polyvinylalcohol 61,000 amw | 1% | 0.20 | 9002-89-5 |
| 3 | Polyethylene glycol 300 (PEG) | 30% | 0.32 | 25322-68-3 |
| 4 | Hydroxypropyl-beta-cyclodextrin | 20% | 0.44 | 94035-02-6 |
| 5 | Capryol 90 | 30% | 1.47 | 31565-12-5 |
| 6 | Labrasol | 30% | 0.15 | NA |
| 7 | Captisol | 20% | 0.38 | 182410-00-0 |
| 8 | Labrafac PG | 30% | 0.38 | 438544-49-1 |
| 9 | transcutol | 20% | 0.66 | 111-90-0 |
| 10 | VitE-TPGS | 5% | 1.74 | 30999-06-5 |
| 11 | Tween 80 | 2% | 0.22 | 9005-65-5 |
| 12 | poloxamer 188 | 20% | 0.21 | 9003-11-6 |
| 13 | Gelucire 44/14 | 20% | 1.17 | NA |
| 14 | capmul | 10% | 0.05 | NA |
| 15 | Peceol | 20% | 0.30 | 2549-72-4 |
| 16 | Solutol HS 15 | 10% | 0.52 | 70142-34-6 |
| 17 | Cremophore | 10% | 1.14 | 61791-12-6 |
| 18 | meglumine | 10% | 0.2 | 6284-40-8 |
| 19 | Labrafil 1944CS | 20% | 0.49 | NA |

Discussion

The studies showed that the test article exhibited fairly low solubility in aqueous solutions, as well as, a variety of organic solvents. The test article (TS) was found to be freely soluble in 1,4-dioxane and chloroform, in addition, several good excipient mixtures were found that increased the relative solubility compared to normal saline. The three best were identified as: Capryol 90 at 30% in normal saline, VitE-TPGS at 5% in normal saline, Gelucire 44/14 at 20% in normal saline, and Cremophore at 10% in normal saline. Further studies were performed in cell lines using VitE-TPGS with the TS. It was also found that increased solubility was achievable by using larger amounts of VitE-TPGS (amounts up to 20% have been used) or by using a co-solvent with the TPGS in saline.

Example 5

Studies were performed to test activity of single weekly injections of thiostrepton (TS) and gentian violet (GV) using VitE-TPGS as an excipient in a mouse model of mesothelioma. The primary goal of this experiment was to determine the in vivo tumor cytotoxicity of TS/GV when administered in single weekly injections using VitE-TPGS as an excipient compared to the standard formulation which only has DMSO. Additionally, weight changes were monitored in animals receiving the TS/GV/VitE formulation in animals with and in animals without malignant mesothelioma (MM) tumors to investigate toxicity profiles.

Methods

Male FOX-Chase SCID mice were injected by intraperitoneal (i.p.) injection with 2.5 million luciferase expressing HM malignant mesothelioma (HM-Luc) tumor cells and tumors were allowed to engraft for 2 weeks. Animals were divided into 4 groups of 6 animals:

Groups:

1. 1.5% DMSO/PBS vehicle control
2. 2% VitE/1.5% DMSO/PBS vehicle control, [VitE-TPGS at used at 13 mM, resulted in 4 mg VitE-TPGS delivered per mouse per injection]
3. 20 mg/kg TS+2 mg/kg GV/1.5% DMSO/PBS
4. 20 mg/kg TS+2 mg/kg GV/2% VitE-TPGS/1.5% DMSO/PBS Following 2 weeks of tumor engraftment, tumors were imaged every Monday using an IVIS live animal imager following i.p. injection of luciferin. Vehicle or drug solutions (200 μL) were injected i.p on Tuesdays for 4.5 weeks. Animals received a total of 4 drug injections. Animals were harvested 42 days post tumor injection due to significant weight loss in vehicle control groups.

Results

Figure 3:
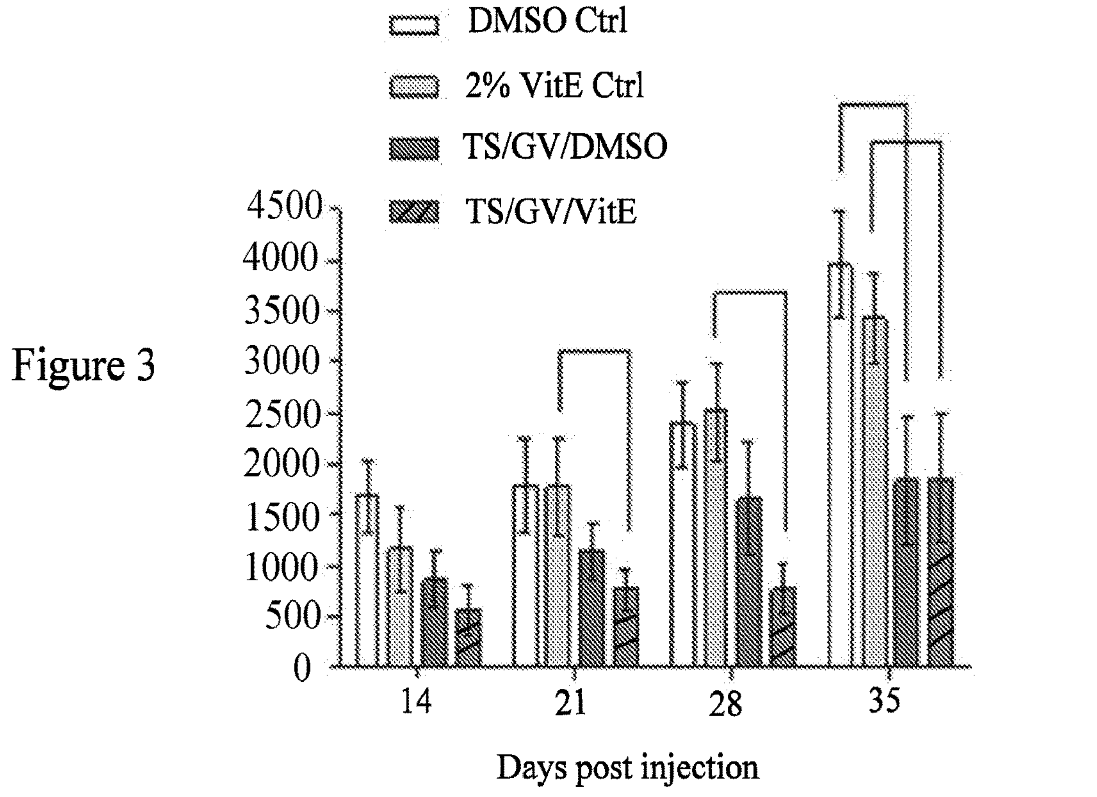
FIG. 3 provides a histogram showing tumor burden assessed by luciferase imaging of in vivo tumors. TS/GV treated animals had tumors ~50% smaller compared to control animals at 35 DPI. (* p<0.05, * p<0.001, ** p<0.0001, 2way ANOVA with Tukey's multiple comparisons test between groups. N=6 animals per group)

Tumors were visualized in animals following i.p. injection of luciferin and live animal imaging on days post injection (DPI) 14, 21, 28 and 35. DPI 21, 28 and 35 correspond to tumor size after 1, 2 or 3 single weekly injections of test compounds. There was no significant difference in tumor size between groups, as assessed by live animal imaging, prior to initiating drug injections (DPI 14). Tumors in both the DMSO and VitE control groups grew at similar rates over the course of the experiment (FIG. 3). Tumor size was significantly smaller in animals receiving TS/GV/VitE at days 21, 28 and 35 compared to VitE vehicle control animals. At 35 DPI the TS/GV/DMSO animals began to show significantly smaller tumors compared to DMSO control animals. The growth of tumors in animals receiving TS/GV/VitE grew at a slower rate compared to animals receiving TS/GV/DMSO (DPI 14-28), but this did not reach statistical significance by a 2-way ANOVA statistical analysis. Although not statistically significant, tumors in the TS/GV/VitE group were ~50% smaller at 28 DPI compared to the TS/GV/DMSO group, with increased animal number it would be expected this would reach statistical significance.

At approximately 35 DPI, animals in the control groups started to show signs of succumbing to the tumor burden as assessed by physical examination of the animals (i.e., signs of jaundice appearing) and significant weight loss (FIG. 4). By 41 DPI, all animals in the control groups and the TS/GV/DMSO groups had lost significant body weight and showed significant signs of distress which required termination of the experiment at 42 DPI. Animals in the TS/GV/VitE group did not show significant weight loss throughout the experiment, indicating this formulation would be ideal for longer term Kaplan-Meier survival studies (FIG. 4).

Animals were sacrificed by isoflurane overdose and cervical dislocation prior to harvesting of organs (lung, liver, kidney) and residual tumor mass. Tumors were weighed and measured (volume) prior to snap-freezing in liquid nitrogen, fixation in paraformaldehyde or processing for cell culture/tumor organoid growth.

Animals in the DMSO control group had visible jaundice and numerous control animals had 15-60% tumor involvement to the diaphragm, an indication of aggressive tumor growth in this model. All groups had at least 1 animal with bloody ascites in the cavity. Some "clubbing" of the liver was also observed in all groups. No gross observations, independent of diaphragm involvement in control mice, were specific to any group, suggesting tumor burden in all groups was responsible for most observed clinical manifestations.

Surgically resected tumors from the TS/GV/DMSO and TS/GV/VitE treated animals did not reach statistical significance compared to controls but did show a 25% and 33% reduction in tumor mass respectively (FIG. 5). This trend supports increased activity of the TS/GV/VitE formulation compared to the TS/GV/DMSO formulation.

DISCUSSION AND CONCLUSION

Single weekly administrations of TS/GV in a 1.5% DMSO/2% VitE-TPGS solution slowed tumor progression in a fixed-time point xenograft mouse model of mesothelioma. TS/GV/VitE showed limited toxicity (weight loss, gross tissue damage) when administered four times over 4.5 weeks to animals with or without tumor implantation. These results support the use of TS/GV/VitE in future Kaplan-Meier survival studies using mouse models of ovarian and mesothelioma. Additionally, these data provide convincing evidence that TS/GV/VitE retains activity in a mouse model of mesothelioma, has increased potency and reduced off-target toxicity compared to the TS/GV/DMSO formulation and is an appropriate formulation to pursue in the clinic.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated herein in their entirety herein by reference.

What is claimed is:

1. A liquid pharmaceutical composition comprising Thiostrepton (TS), dimethyl sulfoxide (DMSO) and 5-10% (w/w) Vitamin E-TPGS, wherein the composition is suitable for intrapleural administration, and wherein the molar concentration of the TS in the composition is in a range from 1 mM to 5 mM.

2. The liquid pharmaceutical composition of claim 1, wherein the molar concentration of the TS in the composition is 1.5 mM.

3. The liquid pharmaceutical composition of claim 1, further comprising one or more of a pharmaceutically acceptable carrier and excipient.

4. The liquid pharmaceutical composition of claim 1, wherein the composition comprises 5% (w/w) Vitamin E-TPGS.

5. The liquid pharmaceutical composition of claim 1, wherein the molar concentration of the TS in the composition is 1.74 mM.

6. The liquid pharmaceutical composition of claim 1, wherein the composition comprises 6-8% (w/w) Vitamin E-TPGS.

7. The liquid pharmaceutical composition of claim 1, wherein the composition comprises 7% (w/w) Vitamin E-TPGS.

8. The liquid pharmaceutical composition of claim 1, wherein the composition comprises 1.74 mM TS, DMSO and 7% (w/w) Vitamin E-TPGS.

* * * * *